(12) United States Patent
Nauck et al.

(10) Patent No.: US 7,569,540 B2
(45) Date of Patent: *Aug. 4, 2009

(54) METHOD FOR ENHANCED PARENTERAL NUTRITION

(75) Inventors: Michael A. Nauck, Bochum (DE); Fred A. Wagner, Walton, NE (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 919 days.

This patent is subject to a terminal disclaimer.

(21) Appl. No.: 10/842,933

(22) Filed: May 10, 2004

(65) Prior Publication Data

US 2004/0209814 A1    Oct. 21, 2004

Related U.S. Application Data

(63) Continuation of application No. 09/011,940, filed as application No. PCT/US96/13615 on Aug. 22, 1996, now Pat. No. 6,852,690.

(30) Foreign Application Priority Data

Aug. 22, 1995    (DE) ................. 195 30 865

(51) Int. Cl.
*A61K 28/38* (2006.01)
*C12P 21/02* (2006.01)

(52) U.S. Cl. ................. 514/3; 514/14; 514/13; 514/12; 514/23; 530/308; 530/324

(58) Field of Classification Search ........... 514/23, 514/12, 13, 14, 3; 530/308, 324
See application file for complete search history.

(56) References Cited

U.S. PATENT DOCUMENTS

| | | | |
|---|---|---|---|
| 5,116,666 A | 5/1992 | Konno | |
| 5,118,666 A | 6/1992 | Habener | |
| 5,120,712 A | 6/1992 | Habener | |
| 5,364,838 A | 11/1994 | Rubsamen | |
| 5,383,848 A | 1/1995 | Hillman et al. | |
| 5,424,286 A * | 6/1995 | Eng ................. | 514/2 |
| 5,487,898 A | 1/1996 | Lu et al. | |
| 5,512,549 A | 4/1996 | Chen et al. | |
| 5,545,618 A | 8/1996 | Buckley et al. | |
| 5,614,492 A | 3/1997 | Habener | |
| 5,846,937 A | 12/1998 | Drucker | |
| 5,912,229 A | 6/1999 | Thim et al. | |
| 6,006,753 A | 12/1999 | Efendic | |

FOREIGN PATENT DOCUMENTS

| | | |
|---|---|---|
| EP | 0619 322 A2 | 10/1994 |
| WO | WO 91/11457 | 8/1991 |
| WO | WO 93/11799 | 6/1993 |
| WO | WO 93/18785 | 9/1993 |
| WO | WO 97/07814 | 3/1997 |
| WO | WO 97/31943 | 9/1997 |
| WO | WO 97/39031 | 10/1997 |
| WO | WO 98/08531 | 3/1998 |
| WO | WO 98/08873 | 3/1998 |
| WO | WO 98/19698 | 5/1998 |
| WO | WO 98/20895 | 5/1998 |
| WO | WO 99/29336 | 6/1999 |
| WO | WO 99/40788 | 8/1999 |

OTHER PUBLICATIONS

Amland, P.F. et al., Scand. J. Gastroenterol, 20(3):321-324 (1985).
Baer, A.R. et al., Diabetes 34(11):1108-1112 (Nov. 1985).
Guo, Jian-Hwa et al., Drug Development and Industrial Pharmacy, 21(17): 2013-2019 (1995).
Gutniak et al., Diabetes Care 17(9) 1039-1044 (1994).
Gutniack, M. et al., Diabetes Care 19(8):843-848 (Aug. 1996).
Japanese Patent Abstract, JP8268908, Dialog(R) File 351: Derwent WPI 96-514913/199651 (Oct. 1996).
Japanese Patent Abstract, JP5207846 Dialog(R) File 251: Derwent WPI 93-297440/199338 (Aug. 1993).
Leone-Bay, A. et al., J. of Medicinal Chemistry, 38(21):4257-4262 (1995).
Schmidt W. et al., Diabetologia 28(9):704-707 (Sep 1985).

* cited by examiner

*Primary Examiner*—T. D. Wessendorf
(74) *Attorney, Agent, or Firm*—Intellectual Property Dept.

(57) ABSTRACT

A method for improved administration of nutrient is provide. The method includes co- or separate administration of a source of nutrients, especially carbohydrates, and insulinotropic peptides and derivatives, analogs, fragments and the like. The method provides high carbohydrate nutrition while avoiding hyper- and hypo-glycemia and their attendant deleterious effects.

15 Claims, No Drawings

METHOD FOR ENHANCED PARENTERAL NUTRITION

CROSS-REFERENCE TO RELATED APPLICATIONS

This application is a continuation of U.S. patent application Ser. No. 09/011,940, filed Mar. 3, 1999 now U.S. Pat. No. 6,852,690 which is the national stage filing of International Application No. PCT/US96/13615, filed Aug. 22, 1996, which claims the benefit of German National Application No. 195 30 865.4, filed Aug. 22, 1995, each of which is hereby incorporated by reference in their entirety, for all purposes.

BACKGROUND OF THE INVENTION

Patients suffering from a variety of illnesses often need to take nutrition by a route other than through the alimentary canal. Patients requiring surgery, patients in comas, patients with digestive tract illness, patients in shock, and patients undergoing healing processes often receive parenteral administration of carbohydrates along with various combinations of lipids, electrolytes, minerals, vitamins and amino acids. Typically this administration is accomplished by intravenous injection or infusion although subcutaneous, intramuscular, peritoneal or other routes may also be used.

When health care professionals administer parenteral nutrients to patients, they take care to avoid blood sugar overload (hyperglycemia). In many cases, even those involving patients with healthy metabolisms, parenteral nutrition can be accomplished and blood sugar levels appropriately maintained through co-administration of insulin. This administration sometimes, however, has serious drawbacks, since insulin has a short half-life and can cause significant variation in the blood sugar levels. Consequently, in serious cases where patients are to receive a high amount of glucose loading, their blood glucose levels are usually titrated and they receive corresponding infusions of insulin to balance the blood glucose level. This titration procedure is both time consuming and requires a significant expense since the insulin infusion preferably is continuous and has to be controlled by serial blood sugar measurement.

It is well-established that patients suffering from malnourishment benefit greatly from rapid delivery of high amounts of nutrients. Usually, oral routes are used for such nutrition so that the health and function of patients' digestive processes are maintained. When a non-oral route for nutrition must be used, the risk of hyperglycemia and the attendant deleterious effects upon osmolarity, kidney tissue, retinal tissue, blood vessels, and the cardiovascular system are great even if insulin co-administration is practiced. Consequently, the traditional nutrition therapies, which often do not use insulin, call for very low rates of nutrient parenteral administration. When a typical patient receives such parenteral nutrition, the rate of administration is maintained at a low value so that the blood sugar (glucose) level does not exceed the normal physiological range of approximately 60 to 150 mg per dl. These low rates of administration provide an appropriate safety factor to avoid hyperglycemia. Usually, the rates range from 50 to 150 ml per hour of a 5 to 40 wt/wt. % glucose solution.

Nevertheless, nutrition is a fundamental requirement to enable patient healing and sustenance. If patients cannot receive adequate nutrition, as many times occurs with traditional parenteral nutrition, healing takes longer and ancillary problems associated with the patient's primary malcondition often occur. Therefore, there often is a need to deliver parenteral nutrition to a patient at as high a rate as possible while avoiding the deleterious effect of hyperglycemia and avoiding the need for repetitive or continuous insulin administration and titration.

SUMMARY OF THE INVENTION

These and other objects are achieved by the invention which is directed to a composition and method for maximal parenteral nutrition substantially without acute or chronic hyperglycemia. The use of the composition in the method of the invention enables delivery of requisite nutrients to satisfy the caloric demand of a patient's healing tissues while at the same time maintaining an appropriate blood glucose level.

The composition of the invention includes a source of nutrients and an insulinotropic peptide. The source of nutrients directly or indirectly provides carbohydrate after administered. Preferably the source of nutrients includes hexoses, pentoses, alcohols thereof and the like, especially those that are highly soluble in aqueous media. Examples include glucose, fructose, galactose, sorbitol, mannitol, zylitol or any combination thereof. Optionally included can be amino acids, electrolytes, lipids, free fatty acids, monoglycerides, diglycerides, triglycerides, glycerol, salts and minerals. The insulinotropic peptide includes gastric inhibitory peptide and its derivatives, glucagon-like peptides such as GLP-1 (1-37) and GLP-1 (7-36), and their derivatives having insulinotropic activity including functional group modifications such as GLP-1 (1-37) amide. GLP-1 (7-36) amide and GLP-1 (7-36) methyl ester, their peptide sequence fragments such as GLP-1 (7-34), GLP-1 (7-37), GLP-1 (7-36), GLP-1 (7-35), their peptide sequence substitutes such as GLP-1 (7-34) Ala Phe Ala, their peptide sequence deletions such as des (Lys) GLP-1 (7-37) amide, their peptide sequence analogs including those with non-natural amino acid residues, as well as their small organic molecule mimics. The insulinotropic peptide may be a pure single compound, a semi-pure single compound or any mixture of compounds such a mixture of GLP-1 and GIP. The source of nutrients and insulinotropic peptide can be combined in a single aqueous medium or can be contained in separate aqueous media, preferably as a kit. Alternatively, the insulinotropic peptide can be separately formulated in tablet or sustained release matrix form for delivery by a buccal, subcutaneous or other absorption route. The concentrations of nutrients and insulinotropic peptides in the composition are described below.

The method of the invention is accomplished by parenteral mixtures of peptides administration of the source of nutrients and the insulinotropic peptide. The administration can be accomplished by prior combination of the nutrient source and peptide, by their co-administration from separate sources, by their separate but concomitant administration or by their separate and sequential administration with the insulinotropic peptide being administered first. Individual peptide compounds as well as mixtures of peptide compounds as described above can be administered as the insulinotropic peptide. The route of administration for the nutrients can be any parenteral route such as intraperitoneal or intravenous while the route for the insulinotropic peptide can the same as or different from the route for the nutrients. The concentration of the insulinotropic peptide used may be any that will deliver and/or maintain normal blood glucose levels in patients who are receiving the source of nutrients according to the invention. The concentrations of nutrients in the nutrient source are at least the same as that typically used for parenteral feeding and the rate of administration is at least the same but is preferably higher than typically prescribed such as preferably a rate providing up to 1000 g of glucose or its equivalent per patient per day. The appropriate dosage of insulinotropic peptide is determined by its sigmoidal dose-response curve relative to the blood glucose level. Consequently, the administration of insulinotropic peptide follows a threshold/increasing level/plateau regimen and is balanced with the rate of administration of the nutrient source so that a normal glucose blood level is achieved or maintained while delivering the nutrient source at an administration rate that would cause the blood glucose level to exceed its normal range if the insulinotropic peptide were not also present. Preferably, the carbohydrate concentration in the nutrient source is in the range of 2% to 50% glucose or its equivalent by weight relative to the total weight of the source. Preferably, the rate of administration of insulinotropic peptide will be calculated to provide and/or maintain at least intermittent peptide blood levels of from 0.1 pmol to 0.1 mmol per liter of plasma.

DETAILED DESCRIPTION OF THE INVENTION

The present invention is directed to a composition and a method for of parenteral nutrition of a patient, especially carbohydrate nutrition, without causing deleterious fluctuations in the patient's blood glucose level. Substantially more rapid delivery of nutrients is achieved by the invention relative to traditional parenteral nutrition so that the calorie demand of the patient's healing cells is almost always met and blood sugar level of the patient does not substantially vary. These unexpected and important medical effects are achieved through the use of a composition of insulinotropic peptides and nutrients such as carbohydrates, amino acids, lipids, monoglycerides, diglycerides, triglycerides, fatty acids, salts, electrolytes and/or minerals.

Although insulinotropic peptides such as GLP-1, GIP and at least some of their fragments, analogs, derivatives and other similar compounds have been known for some time, their use has been directed solely to patients with diabetes. Their application and effect in non-diabetic persons has not been suggested. Indeed, the suggested use of insulinotropic peptides for treatment of diabetic patients indicates that the insulinotropic peptides would have an insulin stimulating effect at these patients' ordinary glucose blood levels. Based upon this suggestion, it would seem that the difficulties occurring with the nutritional administration of insulin would also occur with nutritional use of insulinotropic peptide. Such use would require blood glucose level titration and continuous monitoring of the peptide delivery.

According to the invention, it has been surprisingly found that exogenous administered insulinotropic peptides do not substantially heighten insulin release in a normal patient when he has a normal (non-diabetic) blood glucose level. Furthermore, it has been found according to the invention that when glucose is administered to a normal (non-diabetic) patient by a non-alimentary route, the normal regulatory pathway and mechanism for endogenous insulinotropic peptide production, release, receptor interaction and/or past receptor events either do not occur or are shunted. It has been found that when such a non-diabetic patient undergoes a change in his blood glucose level so as to exceed his normal value, such as by non-alimentary administration of glucose, an insulin stimulatory effect caused by exogenously administered insulinotropic peptide occurs so as to lower the blood glucose level to a normal value. According to the invention, these discoveries have resulted in a method of high and rapid nutrition that avoids hyperglycemia while also avoiding the dangers of hypoglycemia owing to too much insulin and too little blood glucose.

The insulinotropic peptides are used in combination with the nutritional media to provide parenteral nutrition according to the invention. Stabilization of blood glucose levels is achieved readily and significantly with the exogenous parenteral delivery of the insulinotropic peptides. Especially, insulin secretion during parenteral administration of nutrients is highly regulated in this fashion so that increases in blood glucose are significantly less than would be seen without the presence of the insulinotropic peptide. Because a non-diabetic patient has been found to be refractory to the insulinotropic peptide until the glucose level exceeds the patient's normal fasting blood glucose level, and because it has been found that blood insulin levels continue to rise with increasing blood glucose levels and blood insulinotropic peptide levels up to a plateau, and because the blood insulin levels continue to rise with increasing blood glucose levels even though blood insulinotropic peptide levels are held at the plateau level, the amount of insulinotropic peptide to be administered preferably can be standardized irrespective of the amount of glucose to be delivered. Therefore, relative to a nutritional regimen without the insulinotropic peptides, more glucose or its equivalent can be delivered over a shorter time to a patient and the patient's calorie deficit can be more rapidly and satisfactorily fulfilled by practice of the invention. These results are obtained according to the invention without any corresponding side effects from hyper- or hypoglycemia.

According to the invention, the composition to be administered can include carbohydrates alone, such as, hexoses or pentoses, specific examples of which are glucose (dextrose), fructose, galactose, xylitol, mannitol and sorbitol and the like. Alternatively, the composition can include an indirect source of glucose such as lipids, fatty acids, diglycerides, monoglycerides, glycerol and/or amino acids which would be converted to glucose through gluconeogenesis. Electrolytes and minerals such as sodium chloride, potassium chloride, magnesium sulfate, potassium gluconate, sodium acetate, potassium biphosphate, potassium acetate, multiple vitamins and trace elements such as chromium may also be present. Preferably, the composition includes a soluble carbohydrate source such as glucose or one which can be readily converted by the body to glucose. Preferably, other components included in the composition of the invention include a carrier substance such as human serum albumin as well as electrolytes such as sodium chloride, potassium chloride, magnesium chloride, buffers, stabilizers, and preservatives.

The composition can be delivered by injection or infusion as well as by intramuscular, subcutaneous, intravenous, intrarticular, intraperitoneal, buccal (peptides only), nasal membrane (peptides only) and other non-alimentary routes. The nutrients and insulinotropic peptides can be delivered by the same or different routes. It is especially advantageous to deliver the composition by an intravenous route or to deliver the nutrients by an intravenous route and the insulinotropic peptides by a buccal route.

The concentrations of nutrients present in the composition and their rate of delivery are designed to deliver more calories over a 24-hour period than possible with glucose solutions alone. The typical, standard dextrose or glucose solution for use in well-known i.v. feeding is a 5-40 wt/wt % aqueous glucose solution containing some electrolytes. This standard solution is usually delivered at a rate of 50-100 ml per hour so as to maintain a normal blood glucose level of between 100 and 150 milligrams per deciliter. Although this same blood glucose level is maintained through the method of invention, it is now possible to use more concentrated solutions of nutrients and deliver them at faster rates. In particular, the composition of the invention may contain as much as about 50% by weight glucose or its equivalent. The rate of delivery may also be increased so that a 2%, 5%, 10%, 15%, 25%, 40% or 50% by weight solution of glucose or its equivalent can be delivered to provide up to 1000 gm. of glucose or glucose equivalent per patient per day. Care needs to be taken, of course, so that tissue shock at the site of injection does not occur from the delivery of the highly concentrated solutions.

The blood glucose level is maintained at the normal values according to the invention through the co-administration of the insulinotropic peptides. These peptides may be administered as individual pure or semi-pure compounds or in mixture with each other. Consequently, when the singular and plural terms "insulinotropic peptide or insulinotropic peptides" are used in this application, they are meant to cover all degrees of purity of the peptide as well as the individual forms of the peptides and their mixtures in any combination. Typically, the peptide is delivered so as to provide blood concentrations on the order of picomoles to micromoles per L quantities. The insulinotropic peptides may be combined with the nutrients immediately before administration, may be co-administered with the nutrients by use of a separate vessel for the peptides which leads into a common administration line or separate lines to the patient, or may be combined with the nutrients upon manufacture and stored under appropriate conditions to preserve peptide integrity. Alternatively, the insulinotropic peptides can be formulated into pharmaceutically acceptable absorption tabs or tablets, or sustained release matrices such as in a polylactide-glycolide matrix. These solid forms are designed for short to medium term release and absorption of peptides and are known in the art such as, WO/96/07398. DE 3822459, and "Drug Development and Industrial Pharmacy", 21(17), 2013-2019 (1995), the disclosures of which are incorporated herein by reference.

The particular regimen and amount of insulinotropic peptide or peptides administered to an individual patient will depend upon the judgment of the attending physician and the patient's particular condition. As a guideline, if glucose or its nutritional equivalent is to be delivered at higher rates so as to provide up to about 1000 g of glucose per day to the patient, a corresponding larger amount of one or more insulinotropic peptides would be delivered up to a plateau level of about 3 pmol per kg patient weight per minute. This sigmoidal dose-response curve for the insulinotropic peptide has a threshold level followed by the increasing dosage curve up to a plateau of the foregoing level. The dose-response curve is dependent upon the amount of glucose being administered and upon the blood glucose level of the patient. The patient will be refractory to the insulinotropic peptide effect when his blood glucose level is within his normal range. The sigmoidal dose-response occurs when the blood glucose level exceeds that normal range for the non-diabetic patient. At and above that plateau level, insulin stimulation continues and results in increased insulin levels in the blood but the increase follows the level of blood glucose and not the insulinotropic peptide level.

Preferably, the insulinotropic peptides are maintained in a separate, sterile, solid state until shortly before their use. To be used, the solid insulinotropic peptides are preferably combined with sterile buffered aqueous medium to form concentrations of the insulinotropic peptide in the range of nmol to mmol per L levels. Alternatively, the peptides may be combined with a sustained release matrix such as polylactides, polyglycolides, polycaprolactones, hydrogels, microporous polyurethanes, polyvinylidene acetate and the like which are known to provide sustained release of peptides. These formulations can be manipulated to provide short or medium term release of the peptides. See for example U.S. Pat. No. 5,364,838, U.S. Pat. No. 5,383,848, WO/96/07398, DE 3822459, U.S. Pat. No. 5,487,898,"Drug Development and Industrial Pharmacy", 21 (17), 2013-2019 (1995), "Diabetes Care", Vol. 19(8), 843-848 (1996), "Journal of Medicinal Chemistry", (Vol. 38. pg. 4257-4269) and WO/93/18785, the disclosures of which are incorporated herein by reference.

The formulas for the insulinotropic peptides used according to the invention include all known forms of GLP-1 and GIP (the glucagon-like peptide-1 and the gastric inhibitory peptide) and their derivatives. In particular. GLP-1 can be used according to the invention as well as its derivatives including peptide fragments such as GLP-1 (1-36), GLP-1 (1-37), GLP-1 (7-36), GLP-1 (7-37), GLP-1 (7-34), GLP-1 (7-35), similar versions containing substitutions of amino acids such as GLP-1 (7-34) Ala Phe Ala, deletion sequences such as des (Lys) GLP-1 (7-36) amide, analogs with non-natural amino acid residues (e.g., taurine residue, beta and gamma amino acid residues and D-amino acid residues), C-terminal functional group modifications such as amides, esters, and C-terminal ketone modifications and N-terminal functional group modifications such as acylated amines, Schiff bases and the like as well as exendin, glicentin, amylin antagonists and other derivatives such as are described in EP 512042 (Derwent 91-252609/34), WO9325579A1 (Derwent 94-OO7457/01), WO9318786 (Derwent 93-3220451/40) WO9011296 (Derwent 90-320226/42), U.S. Pat. No. 5,545,618, JP63159323 (Derwent 88-224231/32), U.S. Pat. No. 5,118,666, U.S. Pat. No. 5,120,712, U.S. pat. No. 5,512,549, WO9606628, and EP658568, the disclosures of which are incorporated herein by reference. Also included are traditional small organic molecule mimics of the insulinotropic peptides which fit the insulinotropin receptor sites.

These insulinotropic peptides are known and described in the literature. They can be obtained from natural sources as well as by manufacture using recombinant technology or automated and classical synthesis techniques. In particular, reference is made to PCT patent application no. 94/08125 which describes the synthesis of GLP-1 (7-36) amide by a recombinant biotechnology technique. The purities of the insulinotropic peptides may range from semi-pure to highly pure. Their activities in these various states of purity for example can be obtained through titration according to an assay for quantitative insulin release from isolated B-cells of rat pancreas in a saline glucose solution as is taught by Schmidt in Diabetologia (1985) 28:704-707. The titration will provide an activity unit quotient which would be used as a basis to determine the equivalent amount of semi-pure insulinotropic peptide to be administered relative to the amount of pure insulinotropic peptide.

Stock solutions of the insulinotropic peptide which are useful for practice of the invention include an isotonic salt solution such as 0.9% sodium chloride containing from 0.1 to 5% (volume/volume) of a carrier substance such as human serum albumin along with from 1 nmol to 1 mmol per liter of the insulinotropic peptide such as GLP-1 (7-36) amide. This stock solution can be diluted by a factor of 20 for use in infusion with the nutrient solution. Suitable infusion rates for the insulinotropic peptides will range from 0.01 to 50 pmol of peptide per kg of body weight of patient per minute and preferably in the range of 0.2 to 2.5 pmol of peptide per kg of body weight of patient per minute. The administration rate of glucose co-administered with the insulinotropic peptide, especially preferably, may range up to 1000 g of glucose per day or its equivalent, and/or from about 10 to about 800 g of an amino acid mixture per day.

Patients who are especially suited for treatment according to the present invention include patients with a disturbed glucose metabolism such as insulin resistance but no overt diabetes, as well as patients who for any reason cannot receive nutrition through the alimentary canal. Such patients include surgery patients, comatose patients, patients in shock, patients with gastrointestinal disease, patients with digestive hormone disease, and the like. In particular, obese patients, atherosclerotic patients, vascular disease patients, patients with gestational diabetes, patients with liver disease such as liver cirrhosis, patients with acromegaly, patients with glucocorticoid excess such as cortisol treatment or Cushings disease, patients with activated counterregulatory hormones such as would occur after trauma, accidents and surgery and the like, patients with hypertriglyceridemia and patients with chronic pancreatitis can be readily and suitably nourished according to the invention without subjecting the patient to hypo- or hyperglycemia. In particular, the administration to such a patient aims to provide a therapy to as rapidly as possible deliver the nutritional and caloric requirements to the patient while maintaining his plasma glucose below the so-called renal threshold of about 160 to 180 milligrams per deciliter of glucose in the blood. Although normal patients not having glucose levels just below the renal threshold can also be treated according to the invention as described above, patients with disturbed glucose metabolism such as hyperglycemic patients whose plasma glucose level is just above the renal threshold also find the therapy suitable for their condition. In particular, such patients who have a degree of hyperglycemia below the renal threshold at intermittent intervals can receive a combination treatment of nutrients plus insulinotropic peptides according to any of the following regimens. Normal patients not suffering from such hyperglycemia can also be treated according to any of the following regiments.

Regimen A

The patient will receive a fixed i.v. dose of the insulinotropic peptide such as GLP-1 in an amount between 1 to 2 pmol per kilogram of patient weight per minute. The co-administered i.v. nutrients are titrated to the patient to reach a steady state plasma glucose level of approximately 150 milligrams per deciliter or just below the patient's renal threshold. The insulinotropic peptide and the nutrient composition are separately administered through a common i.v. line.

Regimen B

The patient receives a fixed amount of i.v. nutrients according to the patient's nutritional requirements and the insulinotropic peptide such as GLP-1 (7-37) is titrated starting at about 0.4 pmol pg per kg patient weight per minute to up to an infusion rate just below a maximum of approximately 3 pmol per kg patient weight per minute.

Regimen C

The patient receives a fixed amount of nutrients in a nutritional composition (such as up to 1000 g of glucose per day) in combination with a fixed amount of insulinotropic peptide (such as GLP-1 (7-34) at an infusion rate of 2 pmol per kg patient weight per min.). These are administered through separate or common i.v. infusion lines.

To titrate or otherwise follow the progress of the patient during the initial stages and periodically during the treatment using the composition of the invention, the patient can receive the following workups. The patient's blood sugar will be determined at approximately every two hours in the first day and approximately every six hours thereafter. The patient will have insulin and glucagon blood levels titrated before and under treatment to optionally determine the blood insulin and glucagon levels in the patient. The patient optionally may receive indirect calorimetry to determine the patient's glucose oxidation rate and energy expenditure in order to determine the patient's nutritional need and whether his caloric level needs to be increased, decreased or maintained.

The invention has been fully characterized according to the foregoing description. The following examples and protocols provide detailed embodiments of some aspects of the invention. The invention however is not limited to these embodiments and aspects.

Protocol

Provision of Incretin Stimulation of the Insulin Secretion Through Exogenous GLP-1 (7-36) Amide During Parenteral Nourishment.

The goal of this protocol is to ameliorate the problems associated with: parenteral nourishment. It is very often not possible to infuse a desired amount of glucose even to people with healthy metabolism without provoking hyperglycemia (1). Therefore it is necessary even with non-diabetics to add insulin. This results in many time- and money-consuming control tests and limits glucose uptake.

A possible reason for the insufficient endogenous insulin secretion is the lack of the incretin stimulation. Incretin stimulates the secretion of insulin through the effect of intestinal hormones released after oral glucose intake. This stimulation is much better than the insulin increase caused by increasing plasma concentration of such substrates as glucose and amino acids alone. Two of these incretin hormones from the intestines, GLP-1 (7-37) (i.e., the acid) and GLP-1(7-36) amide, have a very strong glucose-dependent insulinotropic and glucagonostatic effect. High doses of such incretins do not lead to hypoglycemia by healthy people, because those incretins have been found in animal tests to have hardly any influence on insulin secretion at normal (sober) plasma glucose values.

Insulin secretion during parenteral nourishment in the presence of GLP-1(7-36amide) can be controlled such that the plasma glucose increase will be less than without GLP-1. Therefore more glucose can be delivered over a 24 hour period than otherwise. The calorie deficit seen with parenterally nourished patients can be better satisfied.

Part A

The study is conducted as follows. Patients include both sexes between the ages 18 and 75 who are dependent on parenteral nourishment. Patients are excluded if they suffer from acute diseases (i.e., fever), and insulin-dependent diabetes and restricted liver and kidney functions (kreatinin>1.2 mg/dl), pregnancy, anemia (hemoglobin<10 g/dl) and treatments with mechanical breathing support and catecholamines. Every patient participates in one study day.

To begin the study, a constant central venous infusion of glucose/amino acid mixture (Aminomix, Frescnius AG) without the infusion of a triglyceridr suspension should be used to continue the parenteral nourishment already in progress. The dose corresponds to the clinically determined calorie demand of the patient. The plasma concentrations of glucose, free fatty acids, triglycerides, amino acids, insulin.

C-peptide and GLP-1 (7-36amide) levels naturally present should be determined every hour for the next 4 hours in the "steady state". If the glucose concentration in this "steady state" is above 150 mg/dl, a sterile and pyrogene free solution of GLP-1 (7-36 amide) (1.2 pmol/kg/min) should be infused for the next 4 hours and all the above values should be measured again in 1 hour intervals. This dose corresponds to the normal "substitution dose" for the incretin hormone GLP-1 (7-36) amide (0.3-0.4 pmol/kg/min) (2) and the necessary pharmacological dose for type 2 diabetics of 1.2 pmol/kg/min (7,8). The treatment is expected to stimulate the insulin secretion and subsequently normalize the plasma glucose. Supplementing this study are indirect calorometry measurements (Deltratrak, Datex, Finland). Therefore 20 min measurement periods are necessary at the start, after 4 hours and at the end of the GLP-1 (7-36) amide infusion period of 8 hours. It is also possible to determine changes in the substrate utilization (glucose and lipid oxidation, energy consumption) from these measurements.

Part B

Every patient participates in three study days.

To begin the study, a constant central venous infusion of glucose/amino acid mixture (Aminomix, Fresenius AG) without the infusion of a triglycerid suspension should be used to continue the parenteral nourishment already in progress. Placebo, GLP-1 (7-36) amide (0.6 pmol/kg/min) with possible changes up to 1.2 pmol/kg/min according to results of study A and insulin (2 U per hr.) should be infused in a random day order. Plasma glucose concentrations should be determined every half hour for the next 6 hours. The glucose infusion should be increased to reach a "steady state" glucose concentration of 150 mg/dl very fast and kept at this level. To supplement this study glucose, free fatty acids, triglycerides, amino acids, insulin. C-peptide and GLP-1 (7-36 amide) should be measured every hour. Indirect calorometry is preformed at the start and end of the 6 hour period.

For taking blood samples it is necessary to place one peripheral vein catheter besides the central vein catheter. Physiological NaCl is slowly infused to keep the vein "open".

GLP-1 (7-36) amide should be received as a GMP product and should be stored at −30° C. as a sterile stock solution (in 0.9% NaCl with 1% human serum albumin). Samples are taken before infusion, sterile-filtered and tested for bacteria growth and endotoxins with the limulus assay.

Blood samples should be taken at the following time points: 0, 60, 120, 180, 240, 300, 360, 420, 480 (study A) and: 0, 60, 120, 180, 240, 300, 360, 420, 480. 540, 660 and 720 (study B).

The statistical analysis can be done with repeated measurement analysis of variance supplemented by one-way ANOVA and t-tests.

EXAMPLE

A 60-year old patient was fed parenterally because of inflammatory bowel disease. He weighed 75 kg. The parenteral nourishment was delivered by a infusomate through a central vein catheter and consisted of 1.5 liter of a 40% glucose solution to deliver approximately 600 g of glucose in 24 hrs and 1 liter of a 10% commercial amino acid mixture. The blood sugar values achieved without GLP-1 (7-36) amide were between 160 and 190 mg/dl. Then GLP-1 (7-36) amide was administered and the blood glucose value was decreased to about 100 mg/dl even though the patient's high rate of glucose administration was continued.

GLP-1 or GIP may be used as a companion medication. The insulinotropic peptide medicament was prepared by a 20:1 dilution of the following stock solution of peptide using normal saline. A stock solution of GLP-1, containing 50 μg/ml and dissolved in 0.9% NaCl with the addition of human serum albumin (end conc. 1% vol/vol) was prepared. The solution was tested for bacterial contamination and pyrogenes and can be stored for 3 months (frozen at −30 C.).

What is claimed is:

1. A method for non-alimentary nutrition comprising administering by a parenteral route to a patient in need of parenteral nutrition;
   a nutritively effective amount of nutrient composition comprising from about 2% to about 50% glucose or the equivalent thereof; and
   an insulinotropic peptide or peptides selected from the groups consisting of a GLP-1, an exendin, the deletion sequences thereof, the natural and non-natural amino acid substitutes thereof, the C-terminus carboxyamides thereof, the C-terminus ketones thereof, the N-terminus modifications thereof, and any mixture thereof.

2. The method of claim 1, wherein said insulinotropic peptide is an exendin.

3. The method of claim 1, wherein said patient has not been diagnosed with diabetes mellitus.

4. The method of claim 1, wherein said nutrient composition further comprises one or more amino acids, lipids, free fatty acids, mono-, di-, or tri-glycerides, glycerol, electrolytes, salts, minerals, vitamins or any combination thereof.

5. The method of claim 1, wherein said insulinotropic peptide or peptides are administered by infusion at a rate of 0.01 to 50 pmol per kg of body weight of patient per minute.

6. The method of claim 1, wherein said nutrient composition is in a first aqueous medium and said insulinotropic peptide is in a second aqueous medium or a pharmaceutically acceptable solid or gel tab or sustained release matrix.

7. The method of claim 1, wherein said insulinotropic peptide or peptides are administered at a standardized concentration sufficient to provide a plateau level of the insulinotropic peptide or peptides in the patient's blood.

8. The method of claim 1, wherein the said nutrient composition and said insulinotropic peptide or peptides are continuously administered.

9. The method of claim 1, wherein said patient is non-diabetic.

10. The method of claim 1, wherein said nutrient composition and said insulinotropic peptide or peptides are administered intravenously, together.

11. The method of claim 1, wherein said nutrient composition and said insulinotropic peptide or peptides are administered intravenously, separately.

12. The method of claim 1, wherein the administration of said nutrient composition produces a blood glucose level in the patient of from about 60 to 180 mg glucose per deciliter of blood, and the rate of administration is calculated to deliver up to about 1000 g of glucose or its equivalent per patient per day.

13. A method for non-alimentary nutrition comprising administering by a parenteral route to a patient in need of parenteral nutrition;

a nutrient composition to provide from about 600 g to about 1000 g of glucose or the equivalent thereof per 24 hours; and an insulinotropic peptide or peptides selected from the group consisting of a GLP-1, an exendin, the deletion sequences thereof, the natural and non-natural amino acid substitutes thereof, the C-terminus carboxamides thereof, the C-terminus ketones thereof, the N-terminus modifications thereof, and any mixture thereof.

14. The method of claim 13, wherein said insulinotrophic peptide is an exendin.

15. The method of claim 13, wherein said nutrient composition further comprises one or more amino acids, lipids, free fatty acids, mono-, di-, or tri-glycerides, glycerol, electrolytes, salts, minerals, vitamins or any combination thereof.

* * * * *